United States Patent [19]

Mack

[11] Patent Number: 5,730,593
[45] Date of Patent: Mar. 24, 1998

[54] EXCHANGEABLE MAGNET FIXTURE WITH CORRESPONDINGLY SHAPED MOUNTING PLATE FOR ALL CURRENT DENTAL ARTICULATORS

[76] Inventor: Florian A. Mack, Taxisstr. 41, D-80637 München, Germany

[21] Appl. No.: 611,070

[22] Filed: Mar. 5, 1996

[30] Foreign Application Priority Data

Mar. 10, 1995 [DE] Germany .................. 195 08 555.8

[51] Int. Cl.⁶ ............................................ A61C 11/00
[52] U.S. Cl. ............................................ 433/60
[58] Field of Search ............................ 433/54, 57, 60, 433/61, 62, 63, 65

[56] References Cited

U.S. PATENT DOCUMENTS

| | | | |
|---|---|---|---|
| 3,221,408 | 12/1965 | Scullin | 433/60 |
| 3,653,126 | 4/1972 | Hansen | 433/60 |
| 4,058,895 | 11/1977 | Mack et al. | |

FOREIGN PATENT DOCUMENTS

| | | | |
|---|---|---|---|
| 25 11 388 | 5/1976 | Germany . | |
| 25 51 189 | 5/1977 | Germany . | |
| 31 35 122 | 4/1982 | Germany . | |
| 3237229 | 4/1984 | Germany | 433/60 |
| 41 18 140 | 12/1992 | Germany . | |
| 42 35 959 | 4/1994 | Germany . | |
| 4239910 | 6/1994 | Germany | 433/60 |

*Primary Examiner*—Cary E. O'Connor
*Attorney, Agent, or Firm*—Larson & Taylor

[57] ABSTRACT

The invention relates to an exchangeable magnet fixture with correspondingly shaped mounting plate for releasably securing plaster models on the lower frame part and on the upper frame part of a dental articulator, the plaster models in each case being plaster-cast on a mounting plate which has a metal plate with which the mounting plate is held securely on the magnet fixture. The magnet fixture is designed so that it can be used in exchange for the conventional screw connection between the upper frame part or lower frame part and the screw-on mounting plate in the hitherto customary dental articulators.

14 Claims, 2 Drawing Sheets

EXCHANGEABLE MAGNET FIXTURE WITH CORRESPONDINGLY SHAPED MOUNTING PLATE FOR ALL CURRENT DENTAL ARTICULATORS

The present invention relates to an exchangeable magnet fixture with correspondingly shaped mounting plate for all current dental articulators.

Dental articulators of this type, which are described, for example, in German Patent Specifications DE-PS 2,511,388 and DE-PS 3,135,122 from the same Applicant, consist essentially of a lower frame part with the holding device for the mounting plate for the mandibular model, and an upper frame part with the holding device for the mounting plate for the maxillary model.

Dental articulators are used for simulating the movements of the mandible, it being possible for the course of the boundary lines to be reconstructed by means of the individual adjustment possibilities. A precondition for this is that the jaw models are fitted in the articulator with the correct coordinates, i.e. in relation to the cranium.

Two mounting plates are used for this fitting, of which one is secured on the lower frame part and one on the upper frame part of the articulator. The mounting plates are in this respect usually secured by means of screws, two positioning bolts being arranged both on the upper part and on the lower part of the articulator for the purpose of precise positioning in the event of the mounting plates being repeatedly refitted in the articulator, these positioning bolts protruding into corresponding bores in the mounting plates when these mounting plates are put into position. One of the two bores is designed as an oblong hole with elastic walls.

Mounting plates of this type are described, for example, in German Patent Specification DE-PS 2,551,189 from the Applicant.

It is also known to secure the mounting plates on the upper frame part or lower frame part of an articulator by means of magnets. For example, a magnet fixture in the form of a round plate is described in German Offenlegungsschrift DE-OS 4,235,959 from the Applicant. A magnet is firmly embedded in this plate. This magnet holder plate with the embedded magnet is screwed onto the upper frame part or lower frame part of the articulator. On its side facing the mounting plate in the assembled state, the magnet holder plate has profile-like projections which are used for positioning the mounting plate to be secured on said plate, the mounting plate having corresponding profile-like depressions. A metal disk is plaster-cast into the mounting plate, and the mounting plate grips when it is placed in the correct position on the magnet holder plate, with this metal disk on the magnet of the magnet holder plate.

In German Offenlegungsschrift DE-OS 4,118,140, a magnet fixture is described in which a magnet plate is arranged in a removable manner in a ferromagnetic well embedded in the frame. A mounting plate which has an embedded metal plate is arranged on the frame with the aid of positioning bolts in such a way that a repeatable positioning is obtained, and a magnetic securing takes place between the metal plate in the mounting plate and the magnet secured in the frame.

A disadvantage of all these magnet fixtures is that special new articulators are required which have the corresponding fixtures. The hitherto customary articulators with a conventional screw connection between mounting plate and upper frame part or lower frame part of the articulator, which are still used in large numbers, can no longer be used for these magnet fixtures.

The object of the present invention is therefore to make available a magnet fixture with correspondingly shaped mounting plate, which makes it possible to retrofit the hitherto customary articulators, having a conventional screw connection between mounting plate and upper frame part or lower frame part, onto a magnetic fixture.

This object is achieved by virtue of the fact that a magnet fixture is used which, instead of having the conventional fastening screw of the hitherto customary articulators, can be screwed into the hole of this fastening screw, or by using a magnet which can be screwed directly onto the conventional fastening screw. It is not therefore necessary to provide a new articulator, and instead a simple retrofitting of the previous articulator is possible, and only one new magnet fixture with correspondingly adapted mounting plate is used, consisting of a small number of individual parts. In order to permit the retrofitting of various hitherto customary articulators, the mounting plate used with the magnet fixture according to the invention has a plurality of openings for the positioning bolts which are present at different locations in different articulators.

The magnet fixture according to the invention and the correspondingly shaped mounting plate are described in greater detail hereinafter with reference to FIGS. 1 through 4.

Figure 1:
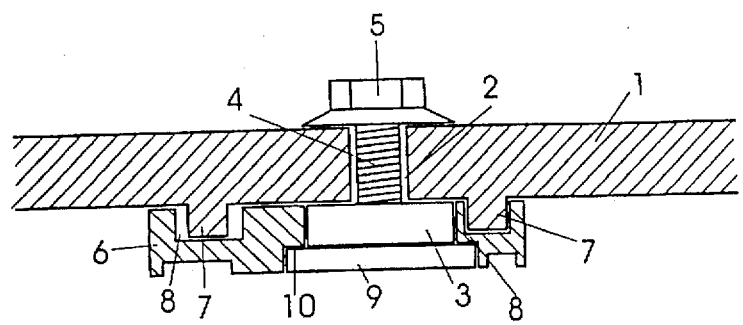
FIG. 1 shows a sectional side view of a magnet fixture according to the invention, with correspondingly shaped mounting plate taken through the line A—A in FIG. 2 in the assembled state.
Figure 5:
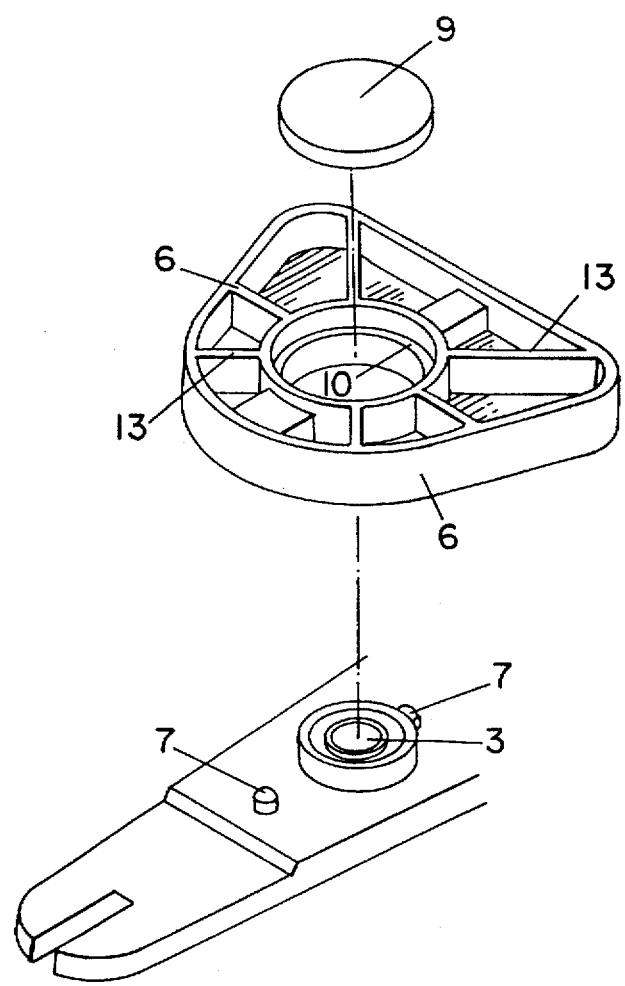
FIG. 5 shows a perspective view of the components of the magnet fixture according to the invention, with a correspondingly shaped mounting plate as represented in FIGS. 2 and 3, before assembly.

FIG. 1 shows the magnet fixture according to the invention with its associated mounting plate in the state when assembled in the articulator. FIG. 5 shows the magnet fixture and its associated mounting plate prior to assembly. The magnet fixture is fitted in the already existing opening 2 in the frame 1 of a hitherto used articulator. In the articulators used hitherto, the opening 2 served for screwing the mounting plate on the upper frame part or lower frame part of the articulator. Now the magnet fixture according to the invention is fitted into this opening. It consists of a magnet 3 of a round or rectangular plate shape. A threaded bolt 4 is arranged securely on this magnet. The magnet 3 is introduced with its threaded bolt 4 through the opening 2 and is screwed from above onto the frame 1 of the articulator using a nut 5. The mounting plate 6 is now guided from underneath onto the magnet fixture in such a way that the positioning bolts 7 normally present on the frame 1 of the articulator engage in the corresponding depressions 8. The positioning of the mounting plate in relation to the upper frame part or lower frame part 1 of the articulator is thus guaranteed to remain the same upon repeated application. It is also possible to provide the magnet with a threaded hole and to screw it onto the upper frame part or lower frame part using a conventional screw, for example the screw already available from the screw connection. When casting the plaster model on, a metal plate 9 is at the same time cast into the mounting plate 6. The metal plate 9 lies on the protruding edge 10 of an opening 11 in the mounting plate. The metal plate 9 is attracted by the magnet 3 and thus holds the mounting plate 6 in a secure but releasable connection on the upper frame part or lower frame part 1 of the articulator.

Figure 2:
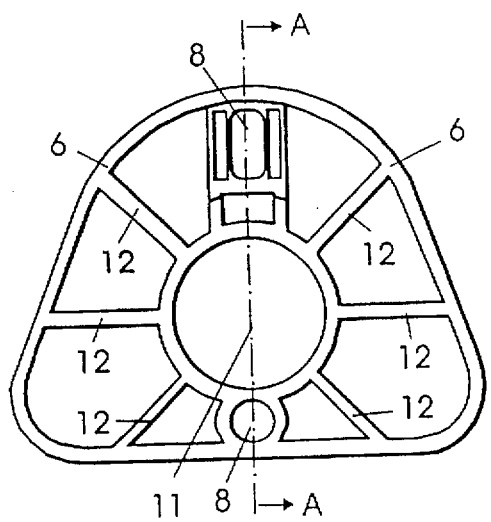
FIG. 2 shows that side of the mounting plate facing the upper frame part or lower frame part of the articulator, which mounting plate is used with the magnet fixture according to the invention.
Figure 3:
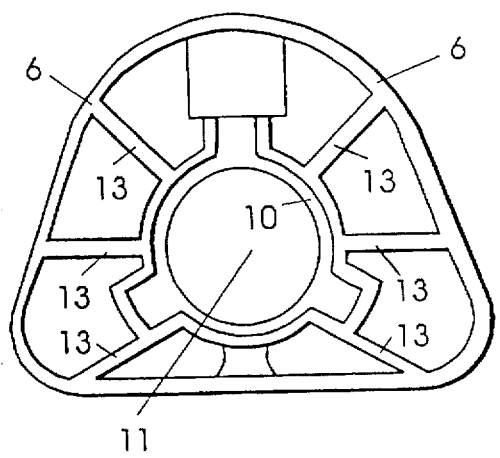
FIG. 3 shows that side of the mounting plate represented in FIG. 2 facing the plaster model, with the depressions for plaster retention.
Figure 4:
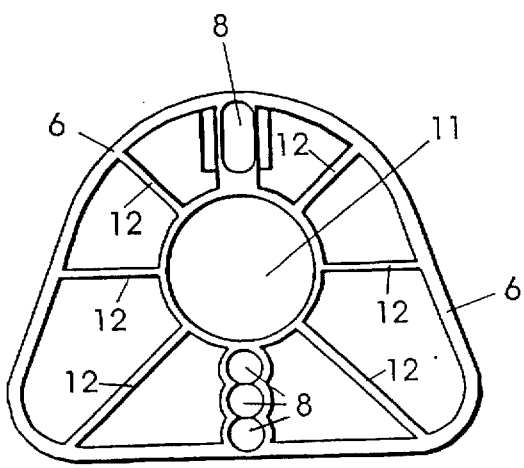
FIG. 4 shows that side of a modified embodiment of the mounting plate facing the upper frame part or lower frame part of the articulator.

FIGS. 2 through 4 show the structures of the mounting plate 6.

FIG. 2 shows a plan view of that side of the mounting plate 6 facing the upper frame part or lower frame part 1 of the articulator. The mounting plate has an opening 11 into which the magnet 3 engages. The opening is shown here as having, by way of example, a circular shape, but it is possible in principle for the openings to have any desired shape, although the shape of the opening and the shape of the magnet have to correspond. The mounting plate has depressions 8 which are used for receiving the positioning bolts arranged on the upper frame part or lower frame part 1 of the articulator. Some of the depressions can also be designed in the shape of an elastic oblong hole which, on the one hand, makes fitting easier and, on the other hand, nevertheless guarantees a secure positioning. The mounting plate is preferably produced in the form of a plastics part and therefore expediently has strengthening ribs 12.

FIG. 3 shows the mounting plate 6 in FIG. 2 from its other side, namely the side facing the plaster model. The peripheral projecting edge 10 can be seen in the opening 11, against which edge 10 the metal plate 9 (not represented here), which is placed into the opening 11 from this side, bears. The mounting plate 6 can be provided on this side with protruding structures 13 which make it easier for the plaster model to be cast on.

FIG. 4 shows a modified embodiment of the mounting plate. It is represented here in the form of a plan view of the side facing the upper frame part or lower frame part of the articulator. In a modification to the embodiment represented in FIG. 2, the embodiment which is represented here has a plurality of adjacent depressions 8 for receiving the positioning bolts which are secured on the frame of the articulator. The depressions can also, if appropriate, have different diameters. As a result of the multiple depressions 8, it is possible for the same mounting plate to be used on articulators with differently placed positioning bolts. This additionally contributes to easier retrofitting of already existing articulators.

Thus, all in all, the invention described herein provides the user with a magnet fixture which he can use in place of the conventional screw connection on hitherto customary articulators. This is a solution which is very practical and easy to implement, since retrofitting is carried out in a very straightforward manner by unscrewing the previous screw connection and introducing the magnet fixture. It is also cost-effective, since the magnet fixture according to the invention and the correspondingly shaped mounting plate consist of only a small number of individual parts.

I claim:

1. An exchangeable magnet fixture with correspondingly shaped mounting plate for releasably securing plaster models on the lower frame part and on the upper frame part of a dental articulator, the plaster models in each case being plaster-cast on a mounting plate having a metal plate with which the mounting plate is held securely on the magnet fixture, the magnet fixture comprising a magnet with an integrally formed threaded bolt which is introduced into an opening of the upper frame part or lower frame part of the articulator, the threaded bolt being secured at its upper end by means of a nut on the upper frame part or the lower frame part, the mounting plate having an opening which receives the magnet so that the metal plate arranged in the mounting plate opening makes contact with the magnet.

2. The magnet fixture according to claim 1, wherein the metal plate is supported on an edge inside the opening of the mounting plate.

3. The magnet fixture according to claim 1, wherein the metal plate ends flush with the side facing the plaster model or is recessed in relation to this side.

4. The magnet fixture according to claim 1, wherein the metal plate is connected releasably to the mounting plate.

5. The magnet fixture according to claim 1, wherein the mounting plate includes a large number of depressions for receiving positioning bolts located on the frame of the articulator.

6. The magnet fixture according to claim 1, wherein the mounting plate includes protruding structures on the side facing the plaster model.

7. The magnet fixture according to claim 1, wherein the magnet has a circular disk shape.

8. An exchangeable magnet fixture with correspondingly shaped mounting plate for releasably securing plaster models on the lower frame part and upper frame part of a dental articulator, the plaster models in each case being plaster-cast on a mounting plate having a metal plate with which the mounting plate is held securely on the magnet fixture, the magnet fixture comprising a magnet with a threaded hole which is secured on the upper frame or the lower frame via a conventional screw connection, the mounting plate having an opening which receives the magnet, so that the metal plate arranged in the mounting plate opening makes contact with the magnet.

9. The magnet fixture according to claim 8, wherein the metal plate is supported on an edge inside the opening of the mounting plate.

10. The magnet fixture according to claim 8, wherein the metal plate ends flush with the side facing the plaster model or is recessed in relation to this side.

11. The magnet fixture according to claim 8, wherein the metal plate is connected releasably to the mounting plate.

12. The magnet fixture according to claim 8, wherein the mounting plate includes a large number of depressions for receiving positioning bolts located on the frame of the articulator.

13. The magnet fixture according to claim 8, wherein the mounting plate includes protruding structures on the side facing the plaster model.

14. The magnet fixture according to claim 8, wherein the magnet has a circular disk shape.

* * * * *